(12) United States Patent
Sinnott

(10) Patent No.: US 11,679,442 B2
(45) Date of Patent: Jun. 20, 2023

(54) DRILL BIT AND METHOD FOR MAKING A DRILL BIT

(71) Applicant: MAESTRO LOGISTICS, LLC, Austin, TX (US)

(72) Inventor: M. Mary Sinnott, Logan, UT (US)

(73) Assignee: MAESTRO LOGISTICS, LLC, Austin, TX (US)

( * ) Notice: Subject to any disclaimer, the term of this patent is extended or adjusted under 35 U.S.C. 154(b) by 0 days.

(21) Appl. No.: 16/447,711

(22) Filed: Jun. 20, 2019

(65) Prior Publication Data

US 2019/0388979 A1    Dec. 26, 2019

Related U.S. Application Data

(60) Provisional application No. 62/732,793, filed on Sep. 18, 2018, provisional application No. 62/688,511, filed on Jun. 22, 2018.

(51) Int. Cl.
    *B23B 51/02*    (2006.01)

(52) U.S. Cl.
    CPC ........ *B23B 51/02* (2013.01); *B23B 2251/043* (2013.01); *B23B 2251/40* (2013.01)

(58) Field of Classification Search
    CPC ........ B23B 2251/043; B23B 2251/406; B23B 2251/408; B23B 2251/426; B23B 2251/40; B23B 51/02
    See application file for complete search history.

(56) References Cited

U.S. PATENT DOCUMENTS

| | | | |
|---|---|---|---|
| 180,554 A | 8/1876 | Cubberly | |
| 390,672 A | 10/1888 | Holmes | |
| 472,541 A | 4/1892 | Johnson | |
| 542,223 A | 7/1895 | Johnson | |
| 750,537 A | 1/1904 | Hanson | |
| 1,309,706 A | 7/1919 | Taylor | |
| 1,557,900 A * | 10/1925 | Thompson | B27G 15/00 408/213 |
| 2,322,894 A * | 6/1943 | Stevens | B23B 51/02 408/230 |

(Continued)

FOREIGN PATENT DOCUMENTS

| | | |
|---|---|---|
| CH | 675842 | 11/1990 |
| DE | 41 17 486 | 12/1992 |

(Continued)

*Primary Examiner* — Nicole N Ramos
(74) *Attorney, Agent, or Firm* — Womble Bond Dickinson (US) LLP

(57) ABSTRACT

A drill bit for forming a round hole in a workpiece, includes a cylindrical shank having a longitudinally extending fluted portion with opposed first and second ends, and defining a longitudinal axis about which the shank is rotatable. The fluted portion includes opposed helical flutes formed in the cylindrical surface of the fluted portion of the shank and extending longitudinally along and between the first and second ends of the fluted portion. The helical flutes each define a concave surface intersecting with the cylindrical surface of the shank to form opposed flute edges. The first end of the fluted portion includes a cutting tip intersecting the helical flutes, wherein at least one of the flute edges has a concave cross-section extending from the second end toward the first end of the fluted portion.

14 Claims, 7 Drawing Sheets

(56) References Cited

U.S. PATENT DOCUMENTS

| | | | |
|---|---|---|---|
| 2,404,048 A | 7/1946 | Gepfert | |
| 2,652,083 A * | 9/1953 | Emmons | B27G 15/00 408/211 |
| 3,709,628 A * | 1/1973 | Hibbert | C22C 38/18 408/229 |
| 4,659,264 A | 4/1987 | Friedline | |
| 4,975,003 A | 12/1990 | Hosoi | |
| 5,049,009 A * | 9/1991 | Beck | B23C 5/10 407/54 |
| 5,160,232 A | 11/1992 | Maier | |
| 5,230,593 A * | 7/1993 | Imanaga | B23B 51/02 408/144 |
| 5,288,183 A * | 2/1994 | Chaconas | B23B 51/02 408/211 |
| 5,312,209 A | 5/1994 | Lindblom | |
| 5,387,059 A | 2/1995 | Borzemsky | |
| 5,478,176 A * | 12/1995 | Stedt | B23B 51/02 408/229 |
| 5,553,682 A | 9/1996 | Batliner et al. | |
| 5,628,837 A | 5/1997 | Britzke et al. | |
| 5,800,101 A | 9/1998 | Jindai et al. | |
| 5,876,202 A | 3/1999 | Berlin | |
| 5,897,274 A | 4/1999 | Ogura et al. | |
| 5,967,712 A | 10/1999 | Magill et al. | |
| 6,045,305 A * | 4/2000 | Plummer | B23B 51/02 408/226 |
| 6,050,754 A | 4/2000 | Thomas | |
| 6,071,046 A | 6/2000 | Hecht et al. | |
| 6,126,367 A | 10/2000 | Reed | |
| 6,190,097 B1 | 2/2001 | Thomas | |
| 6,213,692 B1 | 4/2001 | Guehring et al. | |
| 6,267,542 B1 | 7/2001 | Salmon | |
| 6,312,432 B1 | 11/2001 | Leppelmeier | |
| 6,315,504 B1 | 11/2001 | Sekiguchi et al. | |
| 6,443,674 B1 * | 9/2002 | Jaconi | B23B 51/02 408/1 R |
| 6,514,258 B1 | 2/2003 | Brown et al. | |
| 6,602,029 B1 | 8/2003 | George | |
| 6,629,805 B1 | 10/2003 | Eischeid | |
| 6,641,395 B2 | 11/2003 | Kumar et al. | |
| 6,652,203 B1 | 11/2003 | Risen, Jr. | |
| 6,676,342 B2 | 1/2004 | Mast et al. | |
| 6,688,817 B2 | 2/2004 | Borschert et al. | |
| 6,739,809 B2 | 5/2004 | Shaffer | |
| 6,916,139 B2 | 7/2005 | Yanagida et al. | |
| 6,923,602 B2 * | 8/2005 | Osawa | B23B 51/02 408/230 |
| 6,929,434 B2 | 8/2005 | Prokop | |
| 6,959,775 B2 | 11/2005 | Pedersen | |
| 6,976,812 B2 | 12/2005 | Kaneko et al. | |
| 6,988,859 B2 | 1/2006 | Borschert et al. | |
| D523,313 S | 6/2006 | Ellis | |
| D523,398 S | 6/2006 | Ellis | |
| 7,101,125 B2 | 9/2006 | Borschert et al. | |
| 7,140,815 B2 | 11/2006 | George et al. | |
| 7,201,543 B2 | 4/2007 | Muehlfriedel et al. | |
| 7,214,006 B2 * | 5/2007 | Flynn | B23C 5/10 407/53 |
| 7,228,922 B1 | 6/2007 | DeVall | |
| 7,237,986 B2 | 7/2007 | Anjanappa et al. | |
| 7,241,085 B2 | 7/2007 | Frisendahl | |
| 7,252,465 B2 | 8/2007 | Lindblom | |
| 7,267,514 B2 | 9/2007 | Wetzl et al. | |
| 7,296,954 B2 | 11/2007 | Haenle | |
| 7,306,411 B2 | 12/2007 | Mabuchi et al. | |
| 7,311,480 B2 | 12/2007 | Heule et al. | |
| 7,367,758 B2 | 5/2008 | Turrini et al. | |
| 7,401,667 B2 | 7/2008 | Duscha et al. | |
| 7,513,319 B2 | 4/2009 | DeVall | |
| 7,516,686 B2 | 4/2009 | Wang et al. | |
| 7,575,401 B1 | 8/2009 | Garrick et al. | |
| 7,665,935 B1 | 2/2010 | Garrick et al. | |
| 7,722,299 B2 | 5/2010 | Lenander | |
| 7,740,427 B2 | 6/2010 | Heule et al. | |
| 7,789,599 B2 | 9/2010 | Takikawa | |
| 7,832,966 B2 | 11/2010 | Shultz et al. | |
| 7,837,418 B2 | 11/2010 | Lang et al. | |
| 7,892,235 B2 | 2/2011 | Ellis | |
| 7,909,545 B2 | 3/2011 | Volokh | |
| 8,061,938 B2 | 11/2011 | Sampath et al. | |
| 8,162,945 B2 | 4/2012 | Ellis | |
| 8,172,845 B2 | 5/2012 | Ellis | |
| 8,206,067 B2 | 6/2012 | Turrini | |
| 8,215,882 B2 * | 7/2012 | Li | B23B 51/02 408/230 |
| 8,226,654 B2 | 7/2012 | Ranck et al. | |
| 8,408,850 B2 | 4/2013 | George | |
| 8,475,459 B2 | 7/2013 | Ellis | |
| 8,540,463 B2 | 9/2013 | Goulbourne | |
| 8,579,557 B2 | 11/2013 | Arai et al. | |
| 8,628,278 B2 | 1/2014 | Kremer | |
| 8,740,515 B2 | 6/2014 | Thomas et al. | |
| 8,777,949 B2 | 7/2014 | Ranck et al. | |
| 8,801,344 B2 | 8/2014 | Krenzer et al. | |
| 8,814,483 B2 | 8/2014 | Harouche | |
| 8,834,080 B2 | 9/2014 | Kauper | |
| 8,851,808 B2 | 10/2014 | Kitamori et al. | |
| 8,858,134 B2 | 10/2014 | Glimpel et al. | |
| 8,882,411 B2 | 11/2014 | Koike et al. | |
| 9,073,130 B2 | 7/2015 | Kress | |
| 9,078,670 B2 | 7/2015 | Ellis | |
| 9,085,033 B2 | 7/2015 | Hobohm | |
| 9,089,346 B2 | 7/2015 | Schoutens | |
| 9,131,994 B2 | 9/2015 | Heo | |
| 9,199,315 B2 | 12/2015 | Muhlfriedel et al. | |
| 9,333,564 B2 | 5/2016 | Santamarina et al. | |
| 9,352,399 B2 | 5/2016 | Yanagida et al. | |
| 9,403,246 B2 | 8/2016 | Schwaegerl et al. | |
| 9,468,981 B2 | 10/2016 | Qu et al. | |
| 9,539,653 B2 | 1/2017 | Rogalla et al. | |
| 9,579,108 B2 | 2/2017 | Schoutens | |
| 9,662,717 B2 * | 5/2017 | Prom | B23P 15/32 |
| 9,662,803 B2 | 5/2017 | Lampe | |
| 9,668,754 B2 | 6/2017 | Pfeiffer et al. | |
| 9,848,962 B2 | 12/2017 | Moon et al. | |
| 2002/0040813 A1 | 4/2002 | Kleine et al. | |
| 2003/0053874 A1 | 3/2003 | Moore | |
| 2009/0074527 A1 * | 3/2009 | Kamizaki | B23B 51/02 408/230 |
| 2010/0303565 A1 * | 12/2010 | Xiao | C23C 16/27 407/119 |
| 2011/0081215 A1 * | 4/2011 | Nakamura | B23B 51/02 408/230 |
| 2011/0116884 A1 * | 5/2011 | Li | B23B 51/02 408/223 |
| 2011/0170973 A1 * | 7/2011 | Von Puttkamer | B23P 15/32 408/230 |
| 2013/0006248 A1 | 1/2013 | Ellis | |
| 2014/0161546 A1 * | 6/2014 | Shpigelman | B23C 5/10 407/54 |
| 2014/0356083 A1 * | 12/2014 | Budda | B23C 5/10 407/54 |
| 2015/0283625 A1 * | 10/2015 | Sato | B23B 51/02 408/230 |
| 2016/0151842 A1 * | 6/2016 | Bjork | B23B 51/02 408/59 |
| 2018/0084985 A1 | 3/2018 | Saw et al. | |

FOREIGN PATENT DOCUMENTS

| | | |
|---|---|---|
| EP | 0 549 548 | 6/1993 |
| EP | 1 396 303 | 3/2004 |
| JP | S61-226209 | 10/1986 |
| JP | S62-188614 | 8/1987 |
| JP | H 03184707 | 8/1991 |
| JP | H 04244311 | 9/1992 |
| JP | H 05261612 | 10/1993 |
| JP | 2001287110 A * | 10/2001 |
| JP | 2002/166313 | 6/2002 |

* cited by examiner

300

```
┌─────────────────────────────────────────────────────────────┐
│ FORMING OPPOSED HELICAL FLUTES IN A CYLINDRICAL SURFACE OF A │
│ LONGITUDINALLY EXTENDING FLUTED PORTION OF A CYLINDRICAL SHANK│
│ DEFINING A LONGITUDINAL AXIS ABOUT WHICH THE SHANK IS ROTATABLE,│
│ THE OPPOSED HELICAL FLUTES EXTENDING LONGITUDINALLY ALONG AND │
│ BETWEEN FIRST AND SECOND ENDS OF THE FLUTED PORTION, EACH    │
│ HELICAL FLUTE DEFINING A CONCAVE SURFACE INTERSECTING THE    │
│ CYLINDRICAL SURFACE OF THE SHANK TO DEFINE OPPOSED FLUTE EDGES,│
│ AND THE FIRST END OF THE FLUTED PORTION COMPRISING A CUTTING TIP│
│ INTERSECTING THE HELICAL FLUTES                              │
│                                                         302  │
└─────────────────────────────────────────────────────────────┘
                               │
                               ▼
┌─────────────────────────────────────────────────────────────┐
│ REMOVING A PORTION OF AT LEAST ONE OF THE FLUTE EDGES SUCH THAT│
│ THE AT LEAST ONE OF THE FLUTE EDGES HAS A CONCAVE CROSS-SECTION│
│    EXTENDING FROM THE SECOND END TOWARD THE FIRST END OF THE │
│                        FLUTED PORTION                        │
│                                                         304  │
└─────────────────────────────────────────────────────────────┘
```

*FIG. 7*

DRILL BIT AND METHOD FOR MAKING A DRILL BIT

CROSS-REFERENCE TO RELATED APPLICATIONS

This application claims priority to U.S. Provisional Application No. 62/688,511, filed Jun. 22, 2018 and entitled, "A Drill Bit and Method for Making a Drill Bit," and U.S. Provisional Application No. 62/732,793, filed Sep. 18, 2018 and entitled "A Drill Bit and Method for Making a Drill Bit," each of these applications being incorporated by reference herein.

FIELD OF THE DISCLOSURE

The present disclosure relates to a drill bit. More particularly the present disclosure relates to a drill bit for drilling round holes in a workpiece such as organic material.

BACKGROUND

When drilling holes in organic material, e.g., bone, it may be desirable to drill as close to a round hole as possible, even when drilling by hand. The way that conventional drill bits are formed may adversely affect the shape (e.g., roundness) of the hole drilled in the organic material. More particularly, the configuration of the helical flutes formed in the drill bit (i.e., with "sharp" edges along the length of the flutes) may have an adverse effect on the shape of the hole drilled by the bit. That is, unintended lateral loading of the drill bit, for example, may adversely affect the shape of the hole. More particularly, off-axis lateral loading on the drill bit may cause lateral or side cutting of the workpiece by the sharp edges of the helical flutes of the drill bit such that the shape of the hole drilled in the organic material is oblong or otherwise out-of-round. An out-of-round hole in the workpiece may be problematic as it may remove workpiece material that otherwise would be engaged by a fastener. This will, in turn, result in uneven fastening forces when remaining workpiece material defining the out-of-round hole is engaged by the fastener (i.e., a screw). That is, a fastener defining threads, which is engaged with an out-of-round hole may place more of the fastening stress on the portions of the workpiece about the hole with which the threads are engaged, i.e., portions of the hole that are closer in size to the dimension appropriate for the threads of the fastener.

Accordingly, there exists a need for a drill bit and a method for making a drill bit that addresses or solves at least the issues mentioned herein.

BRIEF SUMMARY OF THE DISCLOSURE

The present disclosure relates to a drill bit and a method for making a drill bit which advantageously reduce the problems associated with off-axis loading, e.g., side cutting of convention drill bits.

In some example embodiments, a drill bit may include a cylindrical shank comprising a longitudinally extending fluted portion having first and second ends, and defining a longitudinal axis about which the shank is rotatable, the fluted portion including opposed helical flutes formed in a cylindrical surface of the fluted portion of the shank and extending longitudinally along and between the first and second ends of the fluted portion, the helical flutes each defining a concave surface intersecting with the cylindrical surface of the shank to define opposed flute edges, the first end of the fluted portion comprising a cutting tip intersecting the helical flutes, at least one of the flute edges having a concave cross-section extending from the second end toward the first end of the fluted portion.

In the preceding embodiment, or any combination of preceding embodiments, the at least one concave cross-section of the flute edge may extend toward and intersects with the cutting tip at the first end of the fluted portion.

In the preceding embodiment, or any combination of preceding embodiments, the at least one concave cross-section of the flute edge may extend toward the first end of the fluted portion without intersecting the cutting tip.

In the preceding embodiment, or any combination of preceding embodiments, a helical angle, may be defined between the longitudinal axis and the at least one concave cross-section of the flute edge, is about 20 degrees. In the preceding embodiment, or any combination of preceding embodiments, both flute edges of each of the helical flutes may have a concave cross-section.

In the preceding embodiment, or any combination of preceding embodiments, the at least one concave flute edge may have a sinusoidal cross-section.

In some example embodiments, a method for making a drill bit may include forming opposed helical flutes in a cylindrical surface of a longitudinally extending fluted portion of a cylindrical shank defining a longitudinal axis about which the shank is rotatable, the opposed helical flutes extending longitudinally along and between first and second ends of the fluted portion, each helical flute defining a concave surface intersecting the cylindrical surface of the shank to define opposed flute edges, and the first end of the fluted portion comprising a cutting tip intersecting the helical flutes; and removing a portion of at least one of the flute edges such that the at least one of the flute edges has a concave cross-section extending from the second end toward the first end of the fluted portion.

In the preceding embodiment, or any combination of preceding embodiments, removing a portion of at least one of the flute edges may comprise removing a portion of at least one of the flute edges such that the concave cross-section of the at least one of the flute edges extends toward and intersects with the cutting tip at the first end of the fluted portion.

In the preceding embodiment, or any combination of preceding embodiments, removing a portion of at least one of the flute edges may comprise removing a portion of at least one of the flute edges such that the concave cross-section of the at least one of the flute edges extends toward the first end of the fluted portion without intersecting the cutting tip.

In the preceding embodiment, or any combination of preceding embodiments, forming the opposed helical flutes in the cylindrical surface of the longitudinally extending fluted portion of the cylindrical shank may comprise removing at least a portion of the cylindrical surface of the cylindrical shank to form the opposed helical flutes.

In the preceding embodiment, or any combination of preceding embodiments, removing at least the portion of the cylindrical surface of the cylindrical shank to form the opposed helical flutes may comprise grinding the cylindrical surface of the cylindrical shank at a helical angle, defined between the longitudinal axis and the at least one concave cross-section of the flute edge, using a grinding wheel, and wherein the helical angle is about 20 degrees.

In the preceding embodiment, or any combination of preceding embodiments, removing a portion of at least one of the flute edges may comprise removing a portion of at least one of the flute edges using a round-edged grinding wheel or ball-end mill to form the concave cross-section.

In the preceding embodiment, or any combination of preceding embodiments, removing a portion of at least one of the flute edges may comprise removing a portion of at least one of the flute edges such that the at least one of the flute edges has a sinusoidal cross-section.

These and other features, aspects, and advantages of the present disclosure will be apparent from a reading of the following detailed description together with the accompanying drawings, which are briefly described below. The present disclosure includes any combination of two, three, four, or more features or elements set forth in this disclosure or recited in any one or more of the claims, regardless of whether such features or elements are expressly combined or otherwise recited in a specific aspect description or claim herein. This disclosure is intended to be read holistically such that any separable features or elements of the disclosure, in any of its aspects, should be viewed as intended to be combinable, unless the context of the disclosure clearly dictates otherwise.

BRIEF DESCRIPTION OF THE DRAWINGS

Figure 1:
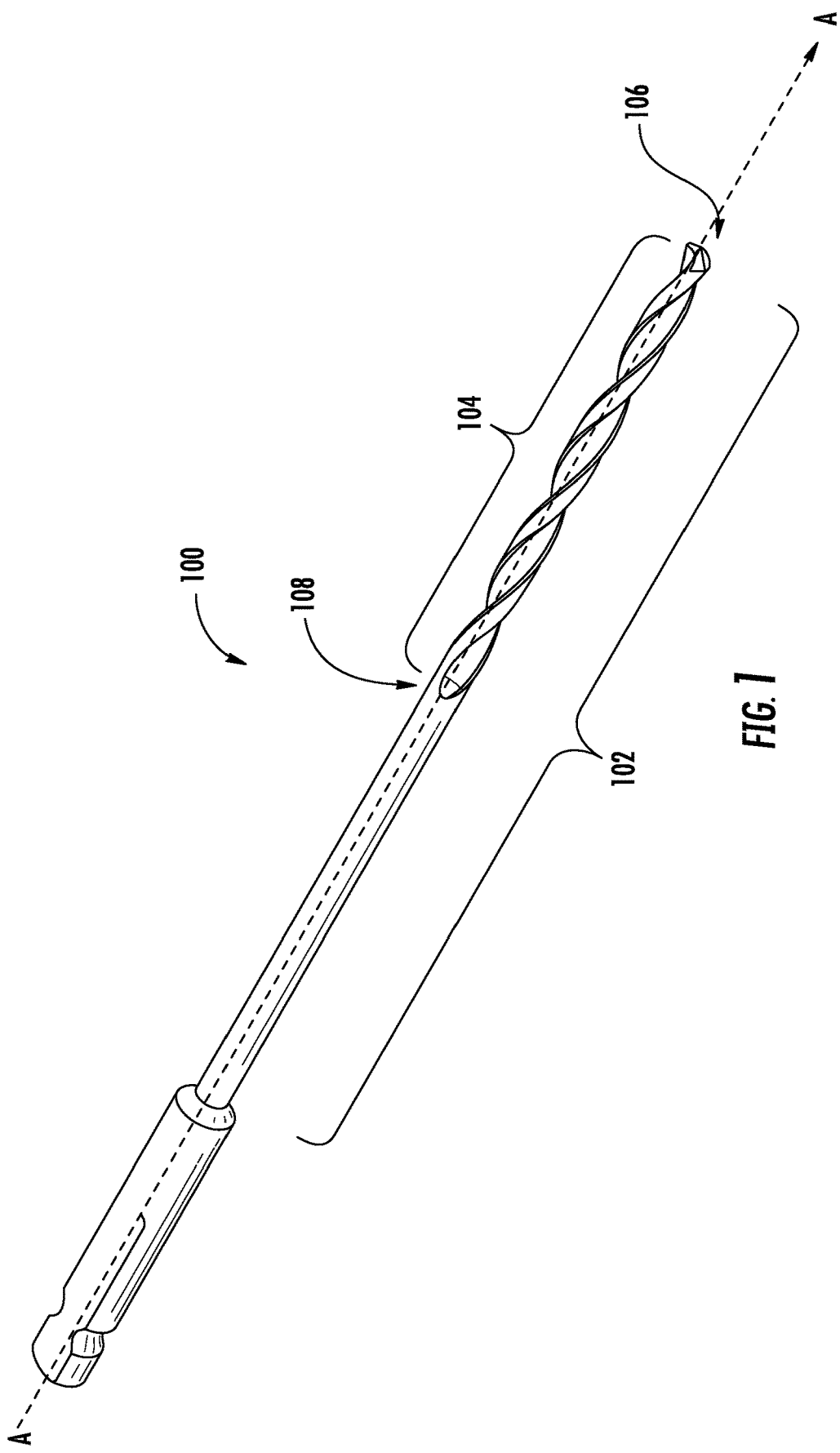
Figure 2:
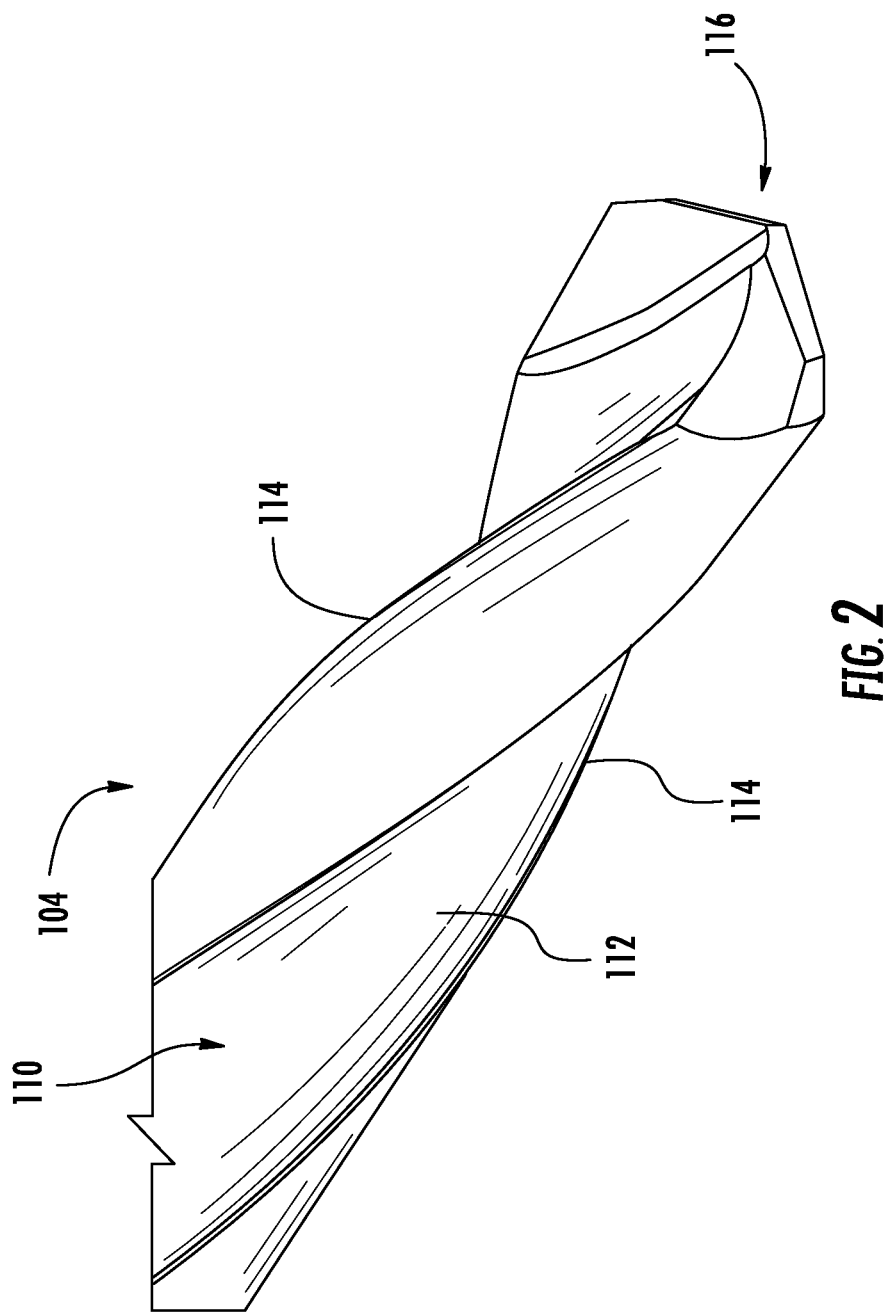
Figure 3A:
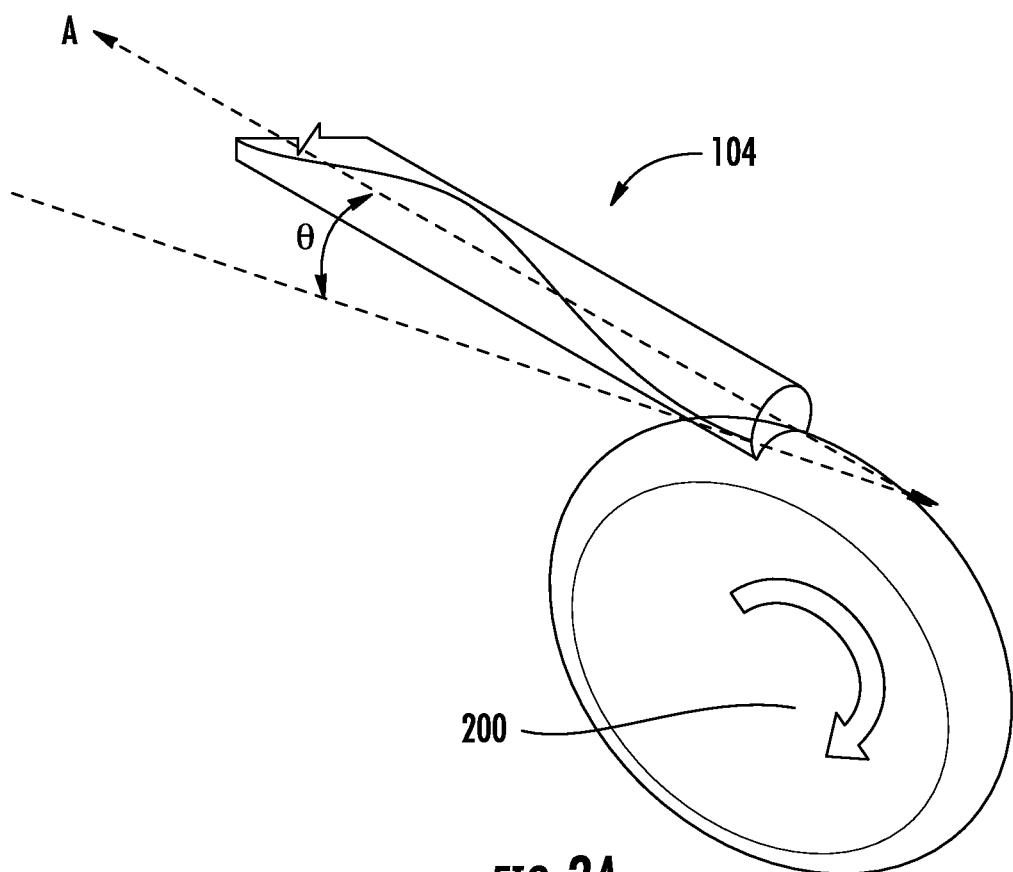
Figure 3B:
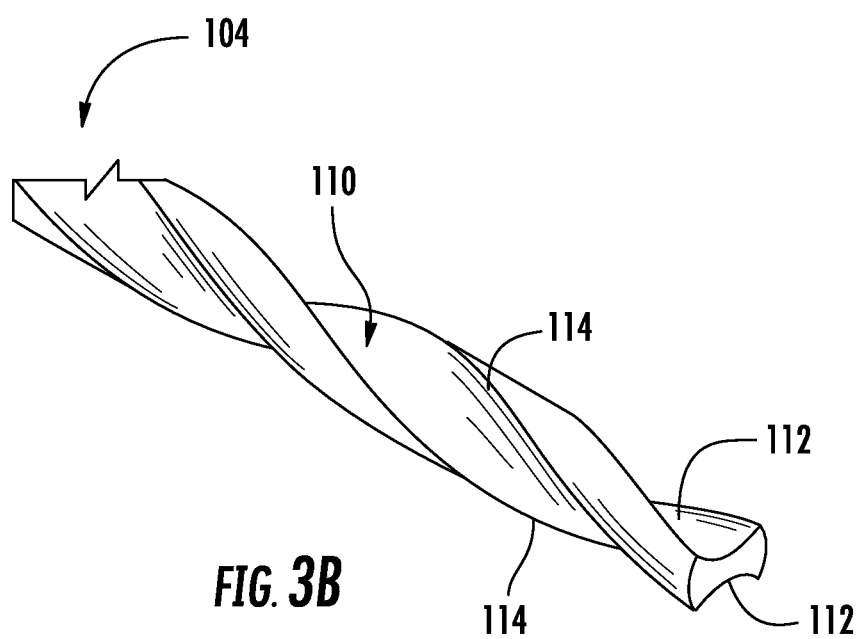
Figure 4A:
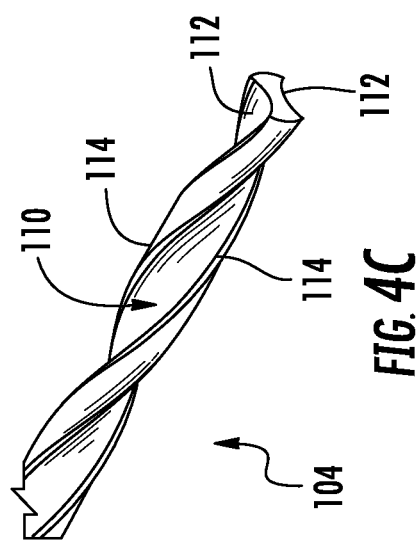
Figure 4D:
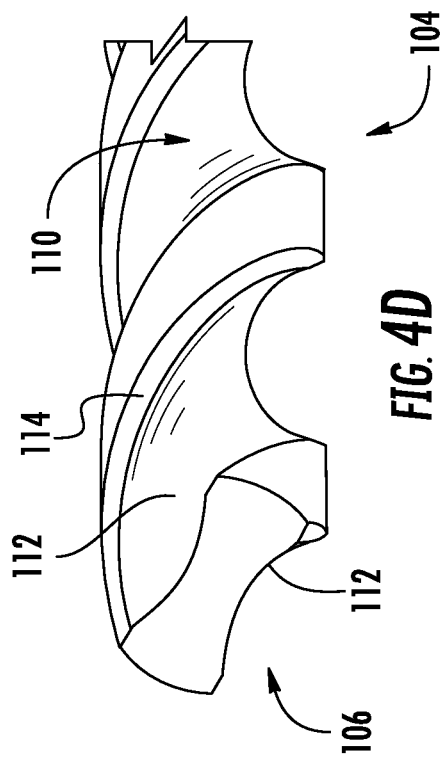
Figure 4C:
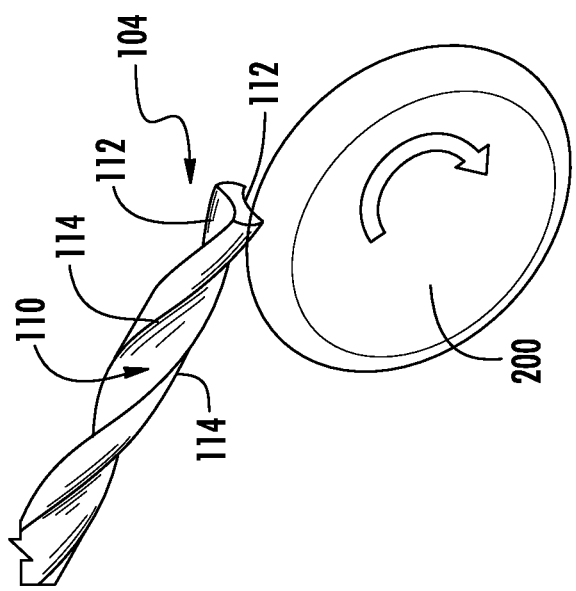
Figure 4B:
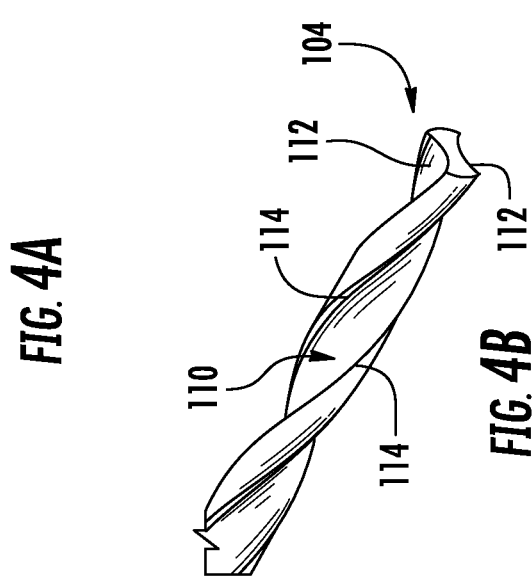
Figure 5A:
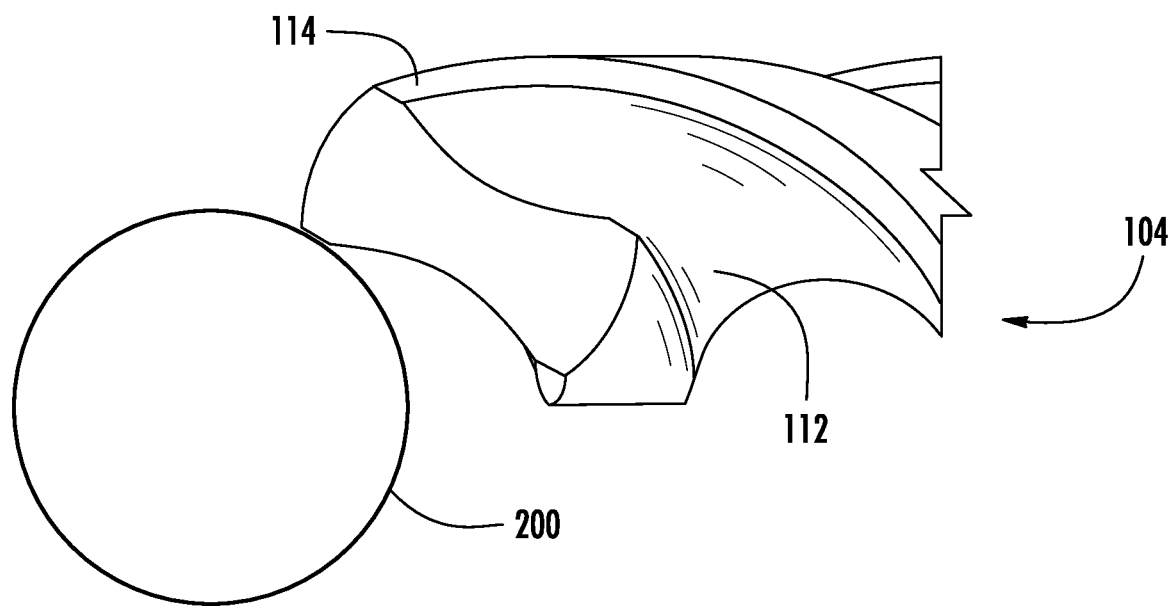
Figure 5B:
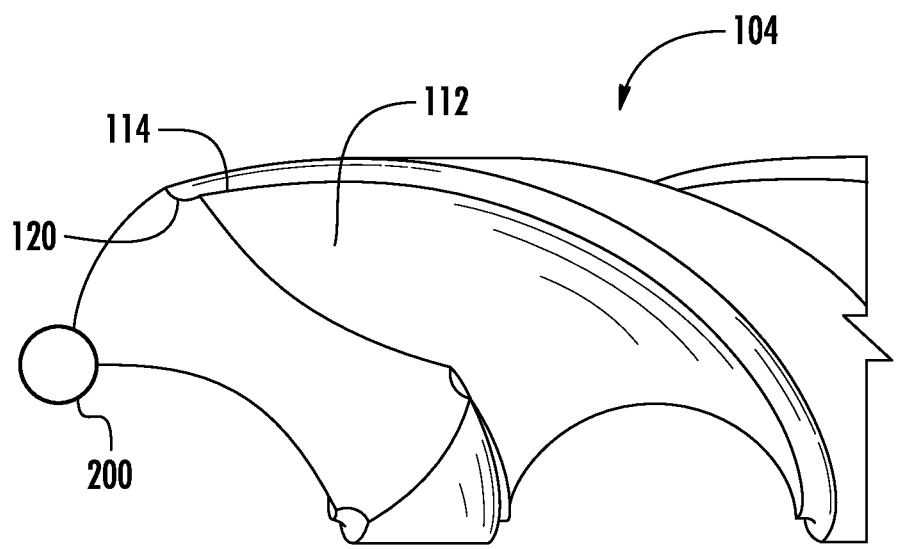
Figure 6:
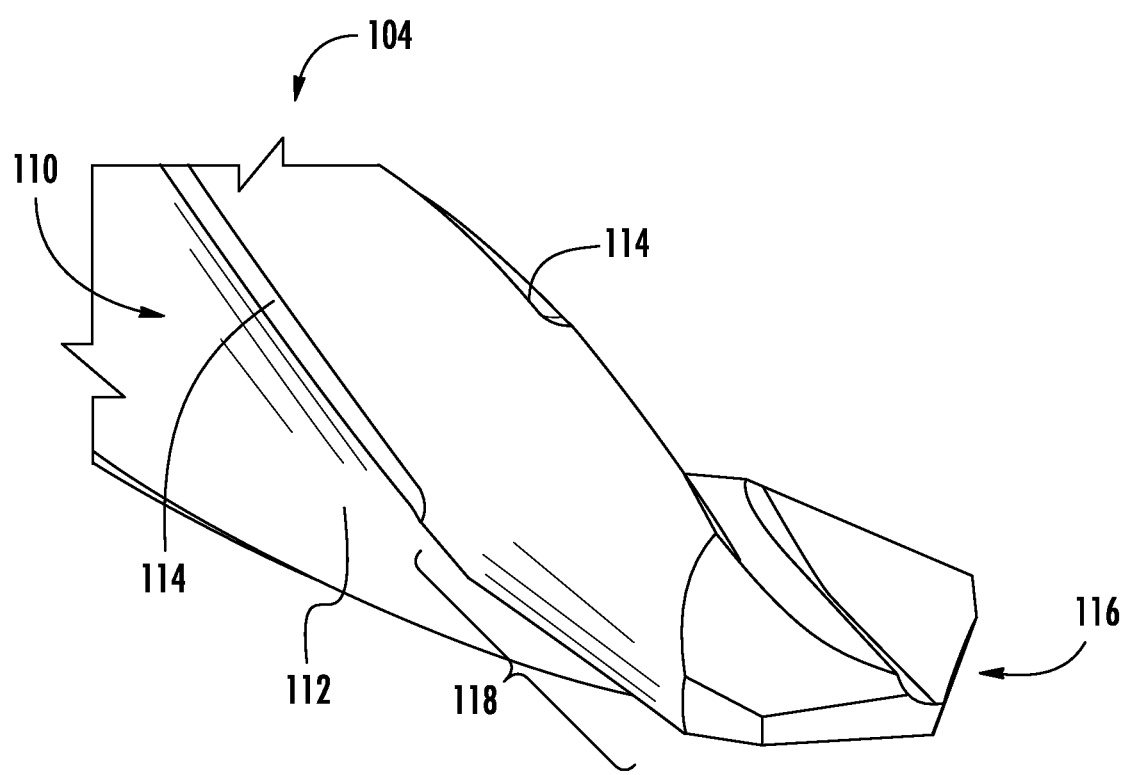

Having thus described the disclosure in general terms, reference will now be made to the accompanying drawings, which are not necessarily drawn to scale, and wherein:

FIG. 1 illustrates a perspective view of an exemplary drill bit according to one aspect of the present disclosure;

FIG. 2 illustrates a perspective view of an exemplary longitudinally extending fluted portion of the drill bit of FIG. 1;

FIG. 3A illustrates a perspective view of an exemplary step of forming helical flutes in a cylindrical surface of a fluted portion of a drill bit according to one aspect of the present disclosure;

FIG. 3B illustrates the helical flutes formed from the exemplary step of FIG. 3A;

FIG. 4A illustrates a perspective view of an exemplary step of removing a portion of at least one of the flute edges in a helical flute of a fluted portion of a drill bit to attenuate the sharpness thereof according to one aspect of the present disclosure;

FIG. 4B illustrates one of the flute edges having the sharpness attenuated in accordance with the exemplary step of FIG. 4A;

FIG. 4C illustrates two of the flute edges having the sharpness attenuated in accordance with the exemplary step of FIG. 4A;

FIG. 4D illustrates all of the flute edges having the sharpness attenuated in accordance with the exemplary step of FIG. 4A;

FIG. 5A illustrates a perspective view of an exemplary step of removing a portion of at least one of the flute edges in a helical flute of a fluted portion of a drill bit to form a concave cross-section of the at least one of the flute edges according to one aspect of the present disclosure;

FIG. 5B illustrates a perspective view of an exemplary step of removing a portion of at least one of the flute edges in a helical flute of a fluted portion of a drill bit to form a concave cross-section of the at least one of the flute edges according to another aspect of the present disclosure;

FIG. 6 illustrates a perspective view of an exemplary longitudinally extending fluted portion including a second embodiment of a cutting tip according to one aspect of the present disclosure; and FIG. 7 illustrates a schematic of an exemplary method for making a drill bit according to one aspect of the present disclosure.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

As disclosed herein, the drill bit of the present disclosure may be utilized for cutting a substantially round hole in a workpiece, such workpiece being formed of organic material (e.g., bone). As such, the drill bit may be termed an orthopedic drill bit; however, other applications for the drill bit disclosed herein are also contemplated.

FIG. 1 illustrates a perspective view of an exemplary drill bit, 100, accordingly to one aspect of the present disclosure. The drill bit may include a cylindrical shank 102 comprising a longitudinally extending fluted portion 104 having opposed first 106 and second ends 108, and defining a longitudinal axis A about which the shank is rotatable. A diameter of the cylindrical shank is variable depending on the application for which the drill bit is being utilized. For example, smaller workpieces requiring smaller holes may necessitate a smaller diameter drill bit, while larger workpieces requiring larger holes may necessitate a larger diameter drill bit. A length of the cylindrical shank may also vary. The length of the fluted portion 104 may also vary. A material of the drill bit may also be variable depending on the application for which it is being utilized. The material of the drill bit may be, for example, surgical grade stainless steel, cobalt chrome, a biocompatible material, or any combination thereof.

A portion of the cylindrical shank 102 comprises the longitudinally extending fluted portion 104, which is illustrated in greater detail in FIG. 2. The longitudinally-extending fluted portion may be disposed at one end of the cylindrical shank, while the opposing end of the cylindrical shank may include a hand grip for manual drilling or a connector for connecting the shank to a chuck of a power drilling device or manual drilling device. The longitudinally-extending fluted portion may be defined by the first end 106 and the opposing second end 108, which together form the bounds of the longitudinally-extending fluted portion (FIG. 1). A length of the longitudinally-extending fluted portion (as well as a length of the shank 102) may vary. Between the first end and the second end thereof, the longitudinally-extending fluted portion may be formed by one of several methods. For example, the longitudinally-extending fluted portion may be formed by removing (e.g., grinding away) at least a portion of the cylindrical surface of the cylindrical shank. In this manner, opposed helical flutes 110 may be formed in the cylindrical surface of the fluted portion of the shank, which extend longitudinally along and between the first and second ends of the fluted portion.

In some aspects, the helical flutes 110 each define a concave surface 112 having opposed edges intersecting with the cylindrical surface of the shank 102 to define opposed flute edges 114. For example, both flute edges of each of the helical flutes may have a concave cross-section. In another example, one of the flute edges may have a sinusoidal cross-section (i.e., the flute edge may have a concave cross-section with the opposing edges of the concavity being radiused or otherwise rounded). Each of these cross-sections may be formed by one or more manufacturing steps that remove the sharpness from or attenuate the sharpness of the flute edges of the helical flutes in order to ameliorate the problems associated with side-cutting by conventional drill bits. The initial step of forming the helical flutes, as illustrated in FIGS. 3A and 3B, automatically creates sharpness on the flute edges of the helical flutes. FIGS. 4A-5B illustrate the additional manufacturing step of blunting or dulling the sharpness of the flute edges and creating concave cross-sections of the flute edges.

More particularly, FIG. 3A illustrates, for example, one exemplary aspect of forming the helical flutes 110 in the cylindrical surface of the fluted portion 104 by grinding the cylindrical surface of the cylindrical shank 102 at a helical angle θ using a grinding wheel 200. The helical angle may be defined between the longitudinal axis A and at least one flute edge 114. FIG. 3B illustrates the helical flutes so formed, where the sharpness of the flute edges is shown. In some aspects, the helical angle is about 20 degrees, though for the same flute pitch, the helical angle will change with a change in the shank (drill bit) diameter.

FIG. 4A illustrates, for example, one aspect of removing a portion of at least one of the flute edges 114. As illustrated in FIG. 4A a grinding wheel 200 may be used on one or both of the flute edges of the opposed helical flutes 110 to remove the sharpness therefrom or otherwise attenuate the sharpness of the flute edge. In some example aspects, the grinding wheel 200 may be used on both of the flute edges simultaneously. FIG. 4B illustrates only one of the flute edges having the sharpness attenuated, while FIG. 4C illustrates both flute edges of one of the helical flutes having the sharpness attenuated. To best avoid side-cutting by the drill bit, it may be most advantageous to attenuate the sharpness of the flute edges of both of the opposed helical flutes. FIG. 4D illustrates a detailed view of a first end 106 of a fluted portion 104 where the sharpness has been attenuated for the flute edges 114 of both of the opposed helical flutes.

Referring back to FIG. 2, in some aspects, the first end of the fluted portion 104 may comprise a cutting tip 116 intersecting the helical flutes 110. In some aspects, the cutting tip is formed from a plurality of cuts relative to the longitudinally-extending fluted portion. For example, an undercut, a primary facet, a secondary facet, and a corner facet may be cut or otherwise formed about an end of the cylindrical shank as illustrated in FIG. 2 to form the cutting tip. As such, the cutting tip is configured to initiate cutting of the hole in the workpiece (i.e., by way of lateral edges formed by the intersection of the cutting tip 116 with the helical flutes 110). The cutting tip in and of itself cutting the workpiece will thus tend to form a substantially round hole, regardless of the angle at which the drill bit 100 is oriented in relation to the workpiece. The cutting tip may be adapted to remove a quantity of material from the workpiece (e.g., organic matter, such as bone), wherein the quantity of material removed from the workpiece by the cutting tip is received by and transmitted along and within the helical flutes toward the second end 108 of the fluted portion for removal of the removed material from the workpiece, in response to rotation of the shank about the longitudinal axis A. In this regard, according to aspects of the present disclosure, at least one of the flute edges 114 may have a concave cross-section extending from the second end 108 toward the first end 106 of the fluted portion 104. In some aspects, one or more of the flute edges has a concave cross-section that extends only a portion of a length of the fluted portion from the second end toward the first end. In other aspects, one or more of the flute edges may have a concave cross-section extending an entire length of the fluted portion from the second end to the first end. A round-edged grinding wheel (e.g., element 200, FIGS. 3A, 4A), a ball-end mill, or the like may be used to form the concave cross-section for the at least one flute edge. Additionally, in some aspects, at least one of the flute edges may have a sinusoidal cross-section (i.e., the flute edge may have a concave cross-section with the opposing edges of the concavity being radiused or otherwise rounded).

FIGS. 5A and 5B illustrate, for example, one aspect of removing a portion of at least one of the flute edges 114 to form the concave cross-section 120. As illustrated in FIGS. 5A and 5B, the round-edged grinding wheel 200 may be used on one or both of the flute edges of each of the opposed helical flutes 110 to attenuate the sharpness thereof. However, a ball-end mill or any other manufacturing device capable of removing a portion of the least one of the flute edges such that the flute edges have a concave cross-section 120 may be used. The round-edged grinding wheel, or other device used, may be applied along an entirety of a length of the flute edge so that an entirety of the flute edge has a concave cross-section 120 or may be applied along only a portion of the flute edge so that only that portion of the flute edge has a concave cross-section 120. Notably, however, each of FIGS. 5A and 5B illustrate grinding wheels 200 of two differing diameters, such that it may be illustrated how a differently sized grinding wheel 200 may affect a geometry of the concave cross-section 120 of the flute edges 114. More particularly, a grinding wheel having a larger diameter may result in a less concave cross-section (FIG. 5A), while a grinding wheel having a smaller diameter may result in a more concave cross-section (FIG. 5B). A desired geometry of the concave cross-section 120 of the flute edges may determine the diameter of the grinding wheel used to form the flute edges.

In FIG. 6, a second embodiment that differs from FIG. 2 illustrates the cutting tip 116 offset from the first end 106 of the fluted portion 104. In some aspects, the at least one flute edge 114 having the concave cross-section extends toward the first end of the fluted portion from the second end 108, without intersecting the cutting tip 116. As illustrated in the example shown in FIG. 6, all of the flute edges are configured with a concave cross-section, and that concave cross-section extends from the second end 108 toward the first end of the fluted portion, but ends in a spaced apart or offset distance 118 from the cutting tip 116 (i.e., the concave cross-section of the at least one flute edge does not intersect with the cutting tip 116). The spaced apart or offset distance of the concave cross-section of the fluted edges 114 from the cutting tip may be between about 2 mm and about 3 mm, although this distance may vary depending on the application for which the drill bit 100 is being used.

As compared with the embodiment illustrated in FIG. 2, the spaced apart or offset relation of the concave cross-section of the flute edges 114 to the cutting tip may advantageously allow for the exemplary drill bit 100 in FIG. 6 to side cut bone in a controlled manner. More particularly, the spaced apart distance 118 of the concave cross-section of the fluted portion 102 may be used to begin side cutting for a specified distance, i.e., whatever the spaced apart distance 118 is, as this spaced apart distance may not be blunted or otherwise dulled. As the drill bit is advanced into a workpiece material along the longitudinally-extending fluted portion 104, the concave cross-section formed on the flute edges 114 at the spaced apart distance 118 from the first end of the fluted portion may then halt the side-cutting and begin forming a round hole. In this manner, the known problems associated with conventional drill bits may be avoided.

FIG. 7 illustrates a method for making a drill bit, such as the drill bit 100 illustrated in FIG. 1. In some aspects, the method 300 includes forming opposed helical flutes in a cylindrical surface of a longitudinally extending fluted portion of a cylindrical shank defining a longitudinal axis about which the shank is rotatable, the opposed helical flutes extending longitudinally along and between first and second ends of the fluted portion, each helical flute defining a concave surface intersecting the cylindrical surface of the shank to define opposed flute edges, with the first end of the fluted portion comprising a cutting tip intersecting the helical flutes (step 302).

In further aspects, the method 300 includes removing a portion of at least one of the flute edges such that the at least one of the flute edges has a concave cross-section extending from the second end toward the first end of the fluted portion (step 304).

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A drill bit comprising:
a cylindrical shank comprising a longitudinally extending fluted portion having first and second ends, and defining a longitudinal axis about which the shank is rotatable, the fluted portion including two opposed helical flutes formed in a cylindrical surface of the fluted portion of the shank and extending longitudinally along and between the first and second ends of the fluted portion, each of the two helical flutes defining a first concave surface intersecting with the cylindrical surface of the fluted portion of the shank, so as to define two opposed flute edges on each of the two helical flutes, the first end of the fluted portion comprising a cutting tip intersecting the helical flutes, wherein each respective flute edge is defined as a second concave surface between the first concave surface of one of the helical flutes and the cylindrical surface of the fluted portion of the shank and at least one of the second concave surfaces of the flute edges extends an entire length of the fluted portion from the second end toward the first end.

2. The drill bit of claim 1, wherein at least one of the second concave surfaces of the flute edges extends toward and intersects with the cutting tip at the first end of the fluted portion.

3. The drill bit of claim 1, wherein the at least one of the second concave surfaces of the flute edges extends toward the first end of the fluted portion without intersecting the cutting tip.

4. The drill bit of claim 1, wherein the second concave surfaces of both of the two flute edges of each of the two helical flutes extend from the second end toward the first end of the fluted portion.

5. The drill bit of claim 1, wherein the at least one concave flute edge has a sinusoidal cross-section.

6. A method for making a drill bit, the method comprising:
forming two opposed helical flutes in a cylindrical surface of a longitudinally extending fluted portion having first and second ends of a cylindrical shank defining a longitudinal axis about which the shank is rotatable, the two opposed helical flutes extending longitudinally along and between the first and second ends of the fluted portion, each of the two helical flutes defining a first concave surface intersecting with the cylindrical surface of the fluted portion of the shank, so as to define two opposed flute edges on each of the two helical flutes, and the first end of the fluted portion comprising a cutting tip intersecting the helical flutes; and
removing a portion of each respective flute edge to define a second concave surface between the first concave surface of one of the helical flutes and the cylindrical surface of the fluted portion of the shank and at least one of the second concave surfaces of the flute edges extends an entire length of the fluted portion from the second end toward the first end.

7. The method of claim 6, wherein removing a portion of each respective flute edge comprises removing a portion of at least one of the flute edges such that at least one of the second concave surfaces of the flute edges extends toward and intersects with the cutting tip at the first end of the fluted portion.

8. The method of claim 6, wherein removing a portion of each respective flute edge comprises removing a portion of at least one of the flute edges such that at least one of the second concave surfaces of the flute edges extends toward the first end of the fluted portion without intersecting the cutting tip.

9. The method of claim 6, wherein removing at least the portion of the cylindrical surface of the cylindrical shank to form the opposed helical flutes comprises grinding the cylindrical surface of the cylindrical shank at a helical angle, defined between the longitudinal axis and the at least one concave cross-section of the flute edge, using a grinding wheel, and wherein the helical angle is about 20 degrees.

10. The method of claim 6, wherein removing a portion of each respective flute edge comprises removing a portion of each respective flute edge using a round-edged grinding wheel or ball-end mill to form the concave cross-section.

11. The method of claim 6, wherein removing each respective flute edge comprises removing a portion of at least one of the flute edges such that the at least one of the concave flute edges has a sinusoidal cross-section.

12. The drill bit of claim 1, wherein an angle, defined between a plane through the longitudinal axis and a plane tangent to the second concave surfaces of the flute edges, is about 20 degrees.

13. The drill bit of claim 1, wherein the second concave surface of at least one of the flute edges is formed by a manufacturing device applied along the entire length of the fluted portion, the manufacturing device having a diameter that corresponds to a concavity of the second concave surface of the at least one of the flute edges along the entire length of the fluted portion.

14. The drill bit of claim 13, wherein the manufacturing device is a rounded edge grinding wheel.

\* \* \* \* \*